US011653943B2

(12) United States Patent
Jadhav

(10) Patent No.: US 11,653,943 B2
(45) Date of Patent: May 23, 2023

(54) DEPLOYMENT MECHANISMS FOR SURGICAL INSTRUMENTS

(71) Applicant: Covidien LP, Mansfield, MA (US)

(72) Inventor: Amarsinh D. Jadhav, Hyderabad (IN)

(73) Assignee: Covidien LP, Mansfield, MA (US)

( * ) Notice: Subject to any disclaimer, the term of this patent is extended or adjusted under 35 U.S.C. 154(b) by 656 days.

(21) Appl. No.: 16/724,973

(22) Filed: Dec. 23, 2019

(65) Prior Publication Data

US 2020/0121344 A1    Apr. 23, 2020

Related U.S. Application Data

(63) Continuation of application No. 15/668,096, filed on Aug. 3, 2017, now Pat. No. 10,517,625, which is a
(Continued)

(51) Int. Cl.
*A61B 18/12* (2006.01)
*A61B 17/29* (2006.01)
(Continued)

(52) U.S. Cl.
CPC ...... *A61B 17/29* (2013.01); *A61B 17/320016* (2013.01); *A61B 18/1445* (2013.01);
(Continued)

(58) Field of Classification Search
CPC ........ A61B 18/1445; A61B 2018/1253; A61B 2018/126; A61B 2018/1455; A61B 2018/1467; A61B 2018/1475
See application file for complete search history.

(56) References Cited

U.S. PATENT DOCUMENTS 5,312,391 A    5/1994  Wilk
5,318,589 A    6/1994  Lichtman
(Continued)

FOREIGN PATENT DOCUMENTS

EP    0908150 A1    4/1999
EP    2679185 A1    1/2014
(Continued)

OTHER PUBLICATIONS

European Search Report completed Jan. 25, 2016 in corresponding European Patent Application No. 15191278, 2 pages.

*Primary Examiner* — Daniel W Fowler
(74) *Attorney, Agent, or Firm* — Carter, DeLuca & Farrell LLP

(57) ABSTRACT

A deployment mechanism for selectively deploying and retracting an energizable member and/an insulative member relative to an end effector assembly of a surgical instrument includes one or more actuators, a clutch assembly, and a drive assembly. The clutch assembly is configured to couple to the actuator(s) to provide rotational motion in the first direction in response to such rotation of the actuator(s) and to decouple from the actuator(s) in response to rotation thereof in the second direction. The drive assembly is operably coupled to the clutch assembly and is configured to convert the rotational motion provided by the clutch assembly into longitudinal motion to translate the energizable member and/or insulative member from a storage position to a deployed position and to translate the energizable member and/or the insulative member from the deployed position back to the storage position.

7 Claims, 11 Drawing Sheets

Related U.S. Application Data continuation of application No. 14/542,858, filed on Nov. 17, 2014, now Pat. No. 9,724,153.

(51) Int. Cl.
| | |
|---|---|
| *A61B 18/14* | (2006.01) |
| *F16H 19/02* | (2006.01) |
| *F16H 19/06* | (2006.01) |
| *F16H 21/32* | (2006.01) |
| *A61B 17/32* | (2006.01) |
| *A61B 17/00* | (2006.01) |
| *A61B 18/00* | (2006.01) |
| *A61B 34/35* | (2016.01) |
| *A61B 90/00* | (2016.01) |
| *A61B 17/28* | (2006.01) |

(52) U.S. Cl.
CPC ............. *F16H 19/02* (2013.01); *F16H 19/06* (2013.01); *F16H 21/32* (2013.01); *A61B 34/35* (2016.02); *A61B 2017/00398* (2013.01); *A61B 2017/2825* (2013.01); *A61B 2017/2901* (2013.01); *A61B 2017/292* (2013.01); *A61B 2017/2902* (2013.01); *A61B 2017/294* (2013.01); *A61B 2017/2912* (2013.01); *A61B 2017/2925* (2013.01); *A61B 2017/2932* (2013.01); *A61B 2017/2938* (2013.01); *A61B 2017/2939* (2013.01); *A61B 2018/0063* (2013.01); *A61B 2018/00083* (2013.01); *A61B 2018/00184* (2013.01); *A61B 2018/00196* (2013.01); *A61B 2018/00791* (2013.01); *A61B 2018/00875* (2013.01); *A61B 2018/126* (2013.01); *A61B 2018/1253* (2013.01); *A61B 2018/1455* (2013.01); *A61B 2018/1467* (2013.01); *A61B 2018/1475* (2013.01); *A61B 2090/065* (2016.02)

(56) References Cited

U.S. PATENT DOCUMENTS

| | | | |
|---|---|---|---|
| 5,324,254 A | 6/1994 | Phillips | |
| 5,401,274 A | 3/1995 | Kusunoki | |
| 5,445,638 A | 8/1995 | Rydell et al. | |
| 5,458,598 A | 10/1995 | Feinberg et al. | |
| 5,556,397 A | 9/1996 | Long et al. | |
| 5,665,100 A | 9/1997 | Yoon | |
| 5,735,873 A | 4/1998 | MacLean | |
| 5,792,164 A | 8/1998 | Lakatos et al. | |
| 5,893,863 A | 4/1999 | Yoon | |
| 5,919,202 A | 7/1999 | Yoon | |
| 6,113,596 A | 9/2000 | Hooven et al. | |
| 6,156,009 A | 12/2000 | Grabek | |
| 6,190,386 B1 | 2/2001 | Rydell | |
| 6,270,497 B1 | 8/2001 | Sekino et al. | |
| 6,299,625 B1 | 10/2001 | Bacher | |
| 6,387,094 B1 | 5/2002 | Eitenmuller | |
| 6,551,313 B1 | 4/2003 | Levin | |
| 6,679,882 B1 | 1/2004 | Komerup | |
| 6,808,525 B2 | 10/2004 | Latterell et al. | |
| 6,942,662 B2 | 9/2005 | Goble et al. | |
| 7,033,356 B2 | 4/2006 | Latterell et al. | |
| 7,063,699 B2 | 6/2006 | Hess et al. | |
| 7,128,254 B2 | 10/2006 | Shelton, IV et al. | |
| 7,232,440 B2 | 6/2007 | Dumbauld et al. | |
| 7,367,976 B2 | 5/2008 | Lawes et al. | |
| 7,402,162 B2 | 7/2008 | Ouchi | |
| 7,445,621 B2 | 11/2008 | Dumbauld et al. | |
| 7,510,562 B2 | 3/2009 | Lindsay | |
| 7,588,570 B2 | 9/2009 | Wakikaido et al. | |
| 7,658,311 B2 | 2/2010 | Boudreaux | |
| 7,758,577 B2 | 7/2010 | Nobis et al. | |
| 7,815,636 B2 | 10/2010 | Ortiz | |
| 7,819,872 B2 | 10/2010 | Johnson et al. | |
| 8,257,352 B2 | 9/2012 | Lawes et al. | |
| 8,353,437 B2 | 1/2013 | Boudreaux | |
| 9,579,117 B2 | 2/2017 | Kappus et al. | |
| 10,517,625 B2 | 12/2019 | Jadhav | |
| 2002/0010485 A1* | 1/2002 | Griego | A61B 17/32056 606/167 |
| 2002/0049442 A1 | 4/2002 | Roberts et al. | |
| 2004/0236326 A1 | 11/2004 | Schulze et al. | |
| 2005/0119655 A1 | 6/2005 | Moses et al. | |
| 2005/0187547 A1 | 8/2005 | Sugi | |
| 2008/0215050 A1 | 9/2008 | Bakos | |
| 2008/0269862 A1* | 10/2008 | Elmouelhi | A61B 18/1492 74/519 |
| 2009/0125026 A1 | 5/2009 | Rioux et al. | |
| 2009/0125027 A1 | 5/2009 | Fischer | |
| 2009/0131974 A1 | 5/2009 | Pedersen et al. | |
| 2009/0254084 A1 | 10/2009 | Naito | |
| 2010/0076430 A1* | 3/2010 | Romero | A61B 18/1445 606/51 |
| 2010/0185196 A1 | 7/2010 | Sakao et al. | |
| 2010/0185197 A1 | 7/2010 | Sakao et al. | |
| 2010/0292690 A1 | 11/2010 | Livneh | |
| 2011/0087218 A1 | 4/2011 | Boudreaux et al. | |
| 2011/0130757 A1 | 6/2011 | Horlle et al. | |
| 2011/0257681 A1* | 10/2011 | Reschke | A61B 17/285 606/206 |
| 2011/0264093 A1 | 10/2011 | Schall | |
| 2011/0276049 A1* | 11/2011 | Gerhardt | A61B 18/1402 606/45 |
| 2012/0022526 A1 | 1/2012 | Aldridge et al. | |
| 2012/0330351 A1 | 12/2012 | Friedman et al. | |
| 2014/0135763 A1 | 5/2014 | Kappus et al. | |
| 2014/0276797 A1 | 9/2014 | Batchelor et al. | |

FOREIGN PATENT DOCUMENTS

| | | |
|---|---|---|
| EP | 2764832 A2 | 8/2014 |
| JP | 4063424 B2 | 3/2008 |

* cited by examiner

DEPLOYMENT MECHANISMS FOR SURGICAL INSTRUMENTS

CROSS-REFERENCE TO RELATED APPLICATIONS

This application is a continuation application of U.S. patent application Ser. No. 15/668,096, filed on Aug. 3, 2017, which is a continuation application of U.S. patent application Ser. No. 14/542,858, filed on Nov. 17, 2014, now U.S. Pat. No. 9,724,153, the entire contents of each of which are incorporated herein by reference.

BACKGROUND

Technical Field

The present disclosure relates to surgical instruments and, more particularly, to deployment mechanisms for deploying, e.g., actuating, one or more components of a surgical instrument.

Background of Related Art

Many surgical instruments include one or more movable handles, levers, actuators, triggers, etc. for actuating and/or manipulating one or more functional components of the surgical instrument. For example, a surgical forceps may include a movable handle that is selectively compressible relative to a stationary handle for moving first and second jaw members of the forceps between spaced-apart and approximated positions for grasping tissue therebetween. Such a forceps may further include a trigger for selectively deploying a knife between the jaw members to cut tissue grasped therebetween.

As can be appreciated, as additional functional components are added to the surgical instrument, additional deployment structures or deployment structures capable of actuating more than one component are required. However, multiple deployment structures and/or combined deployment structures may be limited by spatial constraints within the housing of the surgical instrument, functional constraints of the components (e.g., where a combined deployment structure imparts additional force requirements for deploying one or more of the components coupled thereto), and/or may overly complicate the operable components of the surgical instrument.

SUMMARY

As used herein, the term "distal" refers to the portion that is being described that is further from a user, while the term "proximal" refers to the portion that is being described that is closer to a user. Further, to the extent consistent, any of the aspects described herein may be used in conjunction with any of the other aspects described herein.

Provided in accordance with aspects of the present disclosure is a deployment mechanism for selectively deploying and retracting an energizable member and/or an insulative member relative to an end effector assembly of a surgical instrument. The deployment assembly includes one or more actuators, a clutch assembly, and a drive assembly. The one or more actuators are rotatable in a first direction from an un-actuated position to an actuated position and are rotatable in a second direction from the actuated position back to the un-actuated position. The clutch assembly is associated with the one or more actuators and is configured to couple to the one or more actuators to provide rotational motion in the first direction in response to rotation of the one or more actuators in the first direction. The clutch assembly is further configured to decouple from the one or more actuators in response to rotation of the one or more actuators in the second direction. The drive assembly is operably coupled to the clutch assembly and the energizable member and/or the insulative member. The drive assembly is configured to convert the rotational motion provided by the clutch assembly into longitudinal motion to translate the energizable member and/or the insulative member from a storage position to a deployed position and from the deployed position back to the storage position.

In an aspect of the present disclosure, the clutch assembly includes a clutch gear. In such aspects, the drive assembly includes one or more drive gears operably coupled to the clutch gear for transferring rotational motion of the clutch gear to the at least one drive gear. Further, an intermediate gear may be operably disposed between the clutch gear and the one or more drive gears.

In another aspect of the present disclosure, the clutch assembly includes a first pulley wheel, the drive assembly includes at second pulley wheel, and a pulley belt is operably coupled between the first and second pulley wheels for transferring rotational motion of the first pulley wheel to the second pulley wheel.

In still another aspect of the present disclosure, the drive assembly further includes an arm operably coupled between the clutch assembly and the energizable member and/or the insulative member. The arm is continuously rotatable in one direction such that rotation of the arm through a first portion of a revolution translates the energizable member and/or the insulative member from the storage position to the deployed position, and such that rotation of the arm through a second portion of the revolution translates the energizable member and/or the insulative member from the deployed position back to the storage position.

In yet another aspect of the present disclosure, the deployment mechanism is configured to define a ratio of a degree of rotation of the actuator(s) relative to a degree of rotation of the arm of less than or equal to about 1:3.

In still yet another aspect of the present disclosure, the arm includes a hand disposed at a free end thereof and drive assembly further includes an upright member and a slider. The upright member defines a slot that extends in generally perpendicular orientation relative to an axis of translation of the energizable member and/or the insulative member and the hand of the arm is engaged within the slot. The slider is coupled to the upright member and the energizable member and/or the insulative member. As a result of the above-noted configuration, rotation of the arm in response to the rotational motion provided by the clutch assembly moves the hand along the slot and urges the upright member to translate the slider to thereby translate the energizable member and/or the insulative member from the storage position to the deployed position and to translate the energizable member and/or the insulative member from the deployed position back to the storage position.

In another aspect of the present disclosure, the drive assembly further includes a linkage bar having a first end pivotably coupled to a free end of the arm and a second end, and a slider pivotably coupled to the second end of the linkage bar and coupled to the energizable member and/or the insulative member. As a result of this configuration, rotation of the arm in response to the rotational motion provided by the clutch assembly moves the linkage to translate the slider to thereby translate the energizable member and/or the insulative member from the storage position to the deployed position and to translate the energizable member and/or the insulative member from the deployed position back to the storage position.

In yet another aspect of the present disclosure, the clutch assembly and drive assembly are operably mounted on one or more support members.

In still another aspect of the present disclosure, the one or more support members include a guide configured to guide translation of the energizable member and/or the insulative member between the storage position and the deployed position.

In still yet another aspect of the present disclosure, the one or more support members include at least one locking member configured to releasably lock the energizable member and/or the insulative member in one of the storage position or the deployed position.

Also provided in accordance with aspects of the present disclosure is a surgical instrument including a housing, a shaft extending distally from the housing, an end effector assembly disposed at a distal end of the shaft, a deployable assembly including an energizable member and/or an insulative member that is selectively movable relative to the end effector assembly between a storage condition and a deployed condition, and a deployment mechanism for selectively moving the deployable assembly between the storage condition and the deployed condition. The deployment mechanism may include any of the aspects and features of the deployment mechanism detailed above, and/or any of the other aspects and features detailed herein.

BRIEF DESCRIPTION OF THE DRAWINGS

Various aspects of the present disclosure are described herein with reference to the drawings wherein like reference numerals identify similar or identical elements.

DETAILED DESCRIPTION

Figure 1:
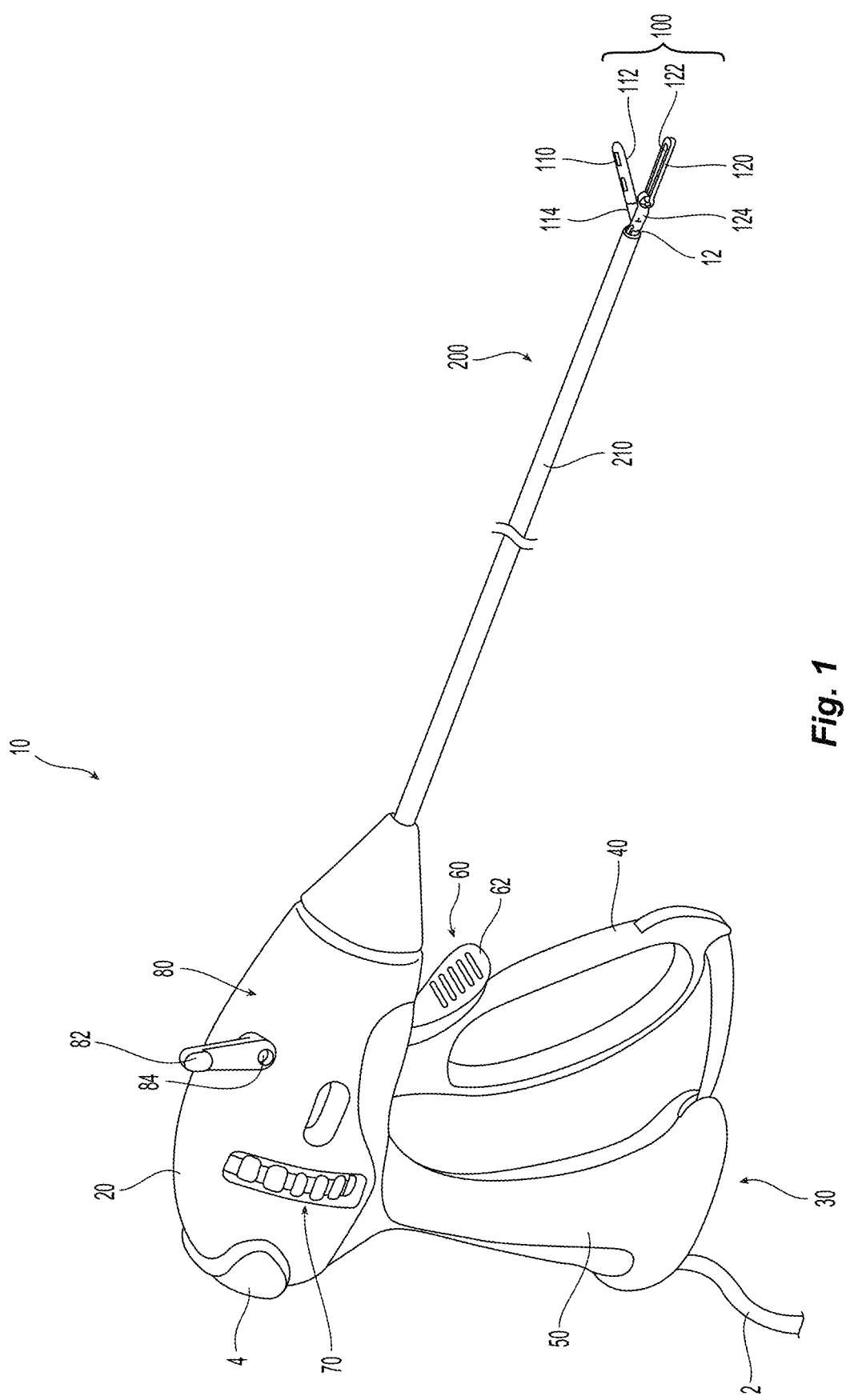
FIG. 1 is a front, perspective view of an endoscopic surgical forceps configured for use in accordance with the present disclosure.

Referring generally to FIG. 1, a forceps provided in accordance with the present disclosure is shown generally identified by reference numeral 10. Forceps 10, as will be described below, is configured to operate in both a bipolar mode, e.g., for grasping, treating, and/or dissecting tissue, and a monopolar mode, e.g., for treating and/or dissecting tissue. Although the present disclosure is shown and described with respect to forceps 10, the aspects and features of the present disclosure are equally applicable for use with any suitable surgical instrument or portion(s) thereof for selectively actuating, moving, and/or deploying one or more assemblies and/or components of the surgical instrument. Obviously, different connections and considerations apply to each particular instrument and the assemblies and/or components thereof; however, the aspects and features of the present disclosure remain generally consistent regardless of the particular instrument, assemblies, and/or components provided.

Continuing with reference to FIG. 1, forceps 10 includes a housing 20, a handle assembly 30, a trigger assembly 60, a rotating assembly 70, a deployment mechanism 80, an end effector assembly 100, and a monopolar assembly 200. Forceps 10 further includes a shaft 12 having a distal end configured to mechanically engage end effector assembly 100 and a proximal end that mechanically engages housing 20. Forceps 10 also includes an electrosurgical cable 2 that connects forceps 10 to a generator (not shown) or other suitable power source, although forceps 10 may alternatively be configured as a battery powered instrument. Cable 2 includes wires (not shown) extending therethrough that have sufficient length to extend through shaft 12 in order to provide electrical energy to at least one of the electrically-conductive surfaces 112, 122 (FIG. 2A) of jaw members 110, 120, respectively, of end effector assembly 100, e.g., upon activation of activation switch 4 in a bipolar mode. One or more of the wires (not shown) of cable 2 extends through housing 20 in order to provide electrical energy to monopolar assembly 200, e.g., upon activation of activation switch 4 in a monopolar mode. Rotating assembly 70 is rotatable in either direction to rotate end effector assembly 100 and monopolar assembly 200 relative to housing 20. Housing 20 houses the internal working components of forceps 10.

Figure 2A:
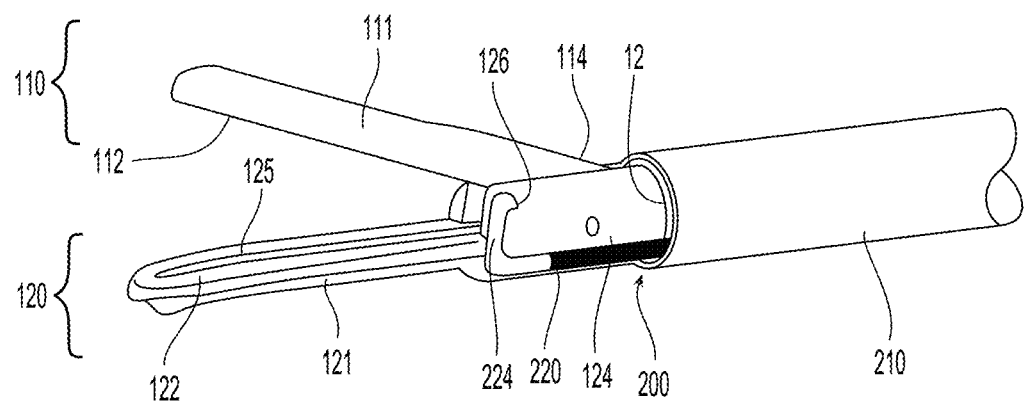
FIG. 2A is an enlarged, front, perspective view of an end effector assembly of the forceps of FIG. 1, wherein jaw members of the end effector assembly are disposed in a spaced-apart position and wherein a monopolar assembly is disposed in a storage condition.
Figure 2B:
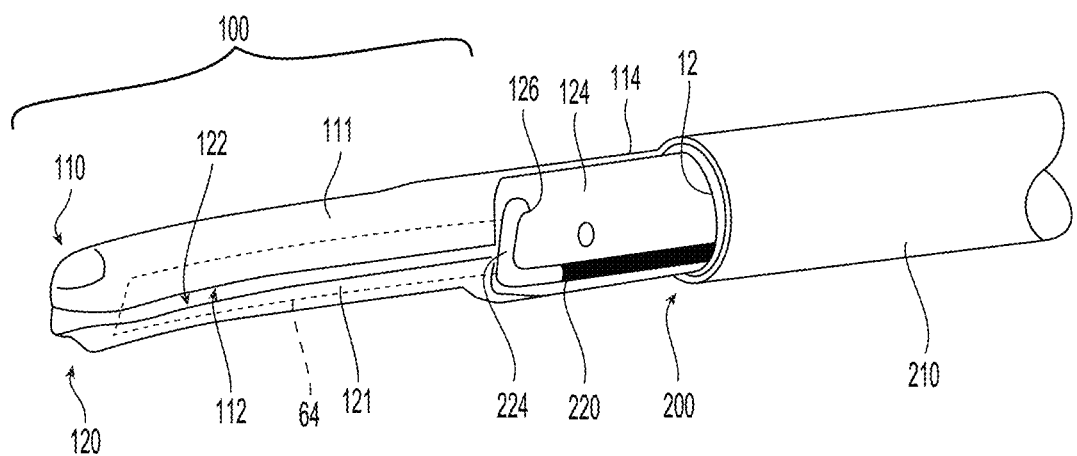
FIG. 2B is an enlarged, front, perspective view of the end effector assembly of FIG. 2A, wherein the jaw members are disposed in an approximated position and wherein the monopolar assembly is disposed in the storage condition.
Figure 2C:
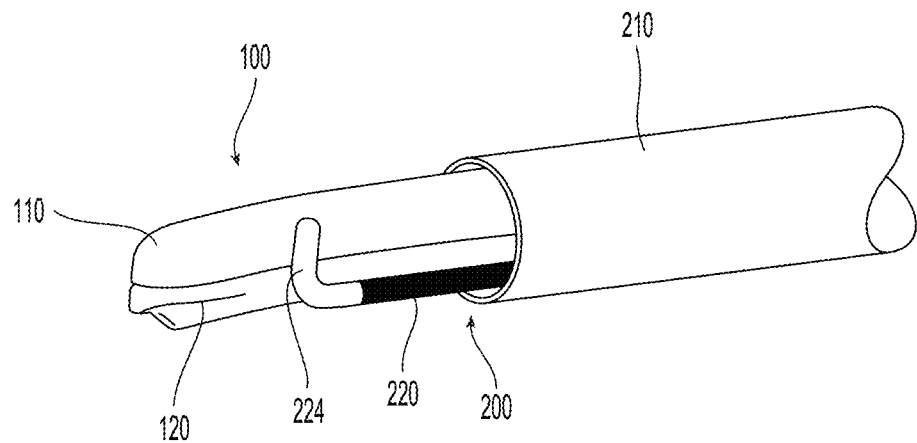
FIG. 2C is an enlarged, front, perspective view of the end effector assembly of FIG. 2B, wherein the jaw members are disposed in the approximated position and wherein the monopolar assembly is transitioning from the storage condition to a deployed condition.

Referring to FIGS. 2A and 2B, end effector assembly 100 is attached at the distal end of shaft 12 and includes opposing jaw members 110, 120 pivotably coupled to one another. Each of the jaw members 110 and 120 includes a jaw body 111, 121 supporting the respective electrically-conductive surface 112, 122, and a respective proximally-extending jaw flange 114, 124. Flanges 114, 124 are pivotably coupled to one another to permit movement of jaw members 110, 120 relative to one another between a spaced-apart position (FIG. 2A) and an approximated position (FIG. 2B) for grasping tissue between surfaces 112, 122. One or both of surfaces 112, 122 are adapted to connect to a source of energy (not shown), e.g., via the wires (not shown) of cable 2 (FIG. 1), and are configured to conduct energy through tissue grasped therebetween to treat, e.g., seal, tissue. More specifically, in some embodiments, end effector assembly 100 defines a bipolar configuration wherein surface 112 is charged to a first electrical potential and surface 122 is charged to a second, different electrical potential such that an electrical potential gradient is created for conducting energy between surfaces 112, 122 and through tissue grasped therebetween for treating e.g., sealing, tissue. Activation switch 4 (FIG. 1) is operably coupled between the source of energy (not shown) and surfaces 112, 122, thus allowing the user to selectively apply energy to surfaces 112, 122 of jaw members 110, 120, respectively, of end effector assembly 100 during a bipolar mode of operation.

End effector assembly 100 is designed as a unilateral assembly, i.e., where jaw member 120 is fixed relative to shaft 12 and jaw member 110 is movable relative to shaft 12 and fixed jaw member 120. However, end effector assembly 100 may alternatively be configured as a bilateral assembly, i.e., where both jaw member 110 and jaw member 120 are movable relative to one another and to shaft 12. In some embodiments, a knife channel 125 may be defined within one or both of jaw members 110, 120 to permit reciprocation of a knife 64 (FIG. 2B) therethrough, e.g., upon actuation of a trigger 62 of trigger assembly 60, to cut tissue grasped between jaw members 110, 120.

Figure 2D:
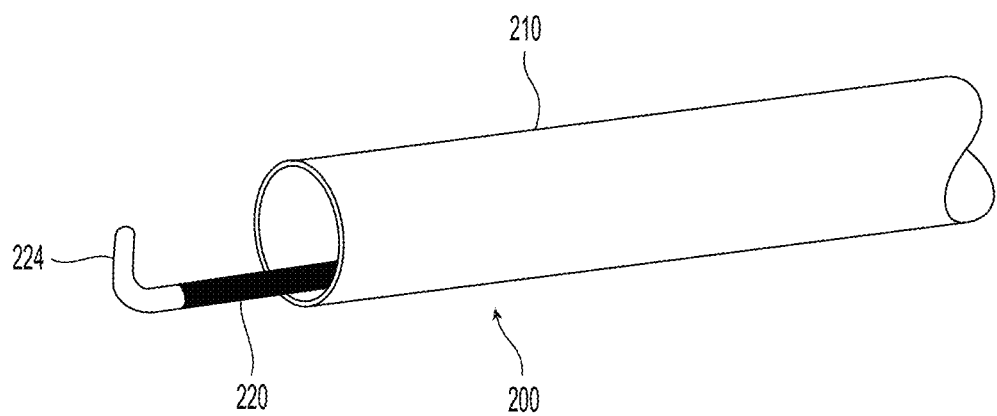
FIG. 2D is an enlarged, front, perspective view of the end effector assembly of FIG. 2B, wherein the monopolar assembly is disposed in the deployed condition.
Figure 3:
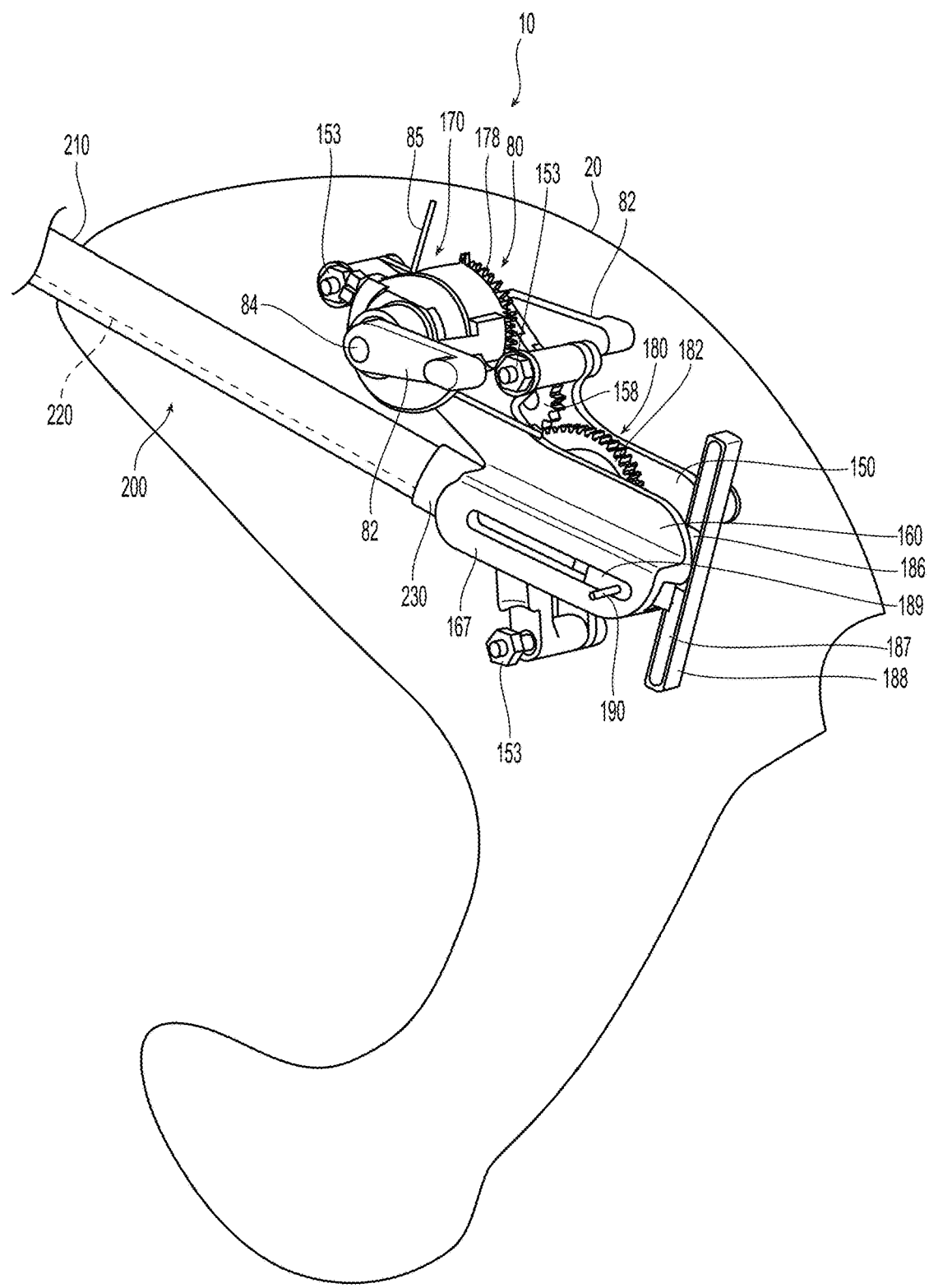
FIG. 3 is a perspective view of the proximal end of the forceps of FIG. 1 with a portion of the housing and internal components thereof removed to unobstructively illustrate a deployment mechanism provided in accordance with the present disclosure.

Referring to FIGS. 1-2D, monopolar assembly 200 includes an insulative sleeve 210, an energizable rod member 220, and a proximal hub 230 (FIG. 3). Insulative sleeve 210 is slidably disposed about shaft 12 and is selectively movable about and relative to shaft 12 and end effector assembly 100 between a storage position (FIGS. 2A and 2B), wherein insulative sleeve 210 is disposed proximally of end effector assembly 100, and a deployed position (FIG. 2D), wherein insulative sleeve 210 is substantially disposed about end effector 100 so as to electrically insulate surfaces 112, 122 of jaw members 110, 120, respectively. With momentary reference to FIG. 3, proximal hub 230 is engaged to insulative sleeve 210 at the proximal end of insulative sleeve 210 and also engages the proximal end of energizable rod member 220. Further, proximal hub 230 is coupled to deployment mechanism 80 (FIGS. 1 and 3) such that, as detailed below, deployment mechanism 80 is selectively actuatable to translate proximal hub 230 along a translation axis through housing 20 and relative to shaft 12 to thereby move monopolar assembly 200 between its storage and deployed conditions (FIGS. 2B and 2D, respectively). The translation axis may be parallel with an axis defined by shaft 12, may be coaxial with the axis of shaft 12, or may be non-parallel relative thereto.

Referring again to FIGS. 1-2D, energizable rod member 220 extends from proximal hub 230 (FIG. 6), through sleeve 210, and distally therefrom, ultimately defining an electrically-conductive distal tip 224. Energizable rod member 220 and, more specifically, distal tip 224 thereof, functions as the active electrode of monopolar assembly 200. The one or more wires (not shown) extending from cable 2 through housing 20 (see FIG. 1), are coupled to energizable rod member 220 to provide energy to energizable rod member 220, e.g., upon actuation of activation switch 4 (FIG. 1) in a monopolar mode, for treating tissue in a monopolar mode of operation. Energizable rod member 220 is movable between the storage position (FIG. 2B) and the deployed position (FIG. 2D). In the storage position (FIG. 2B), distal tip 224 of rod member 220 is disposed within an insulated groove 126 defined within flange 124 of jaw member 120, although other configurations are also contemplated, e.g., distal tip 224 of rod member 220 may simply be positioned alongside flange 124 in the storage condition. Insulated groove 126 electrically-insulates distal tip 224 of rod member 220 from electrically-conductive surfaces 112, 122 of jaw members 110, 120, respectively, and from surrounding tissue when disposed in the storage position. Alternatively, distal tip 224 of rod member 220 may only be insulated from surface 112. In such configurations, distal tip 224 of rod member 220 is capable of being energized to the same polarity as surface 122.

In the deployed position (FIG. 2D), distal tip 224 of rod member 220 of monopolar assembly 200 extends distally from end effector assembly 100 and insulative sleeve 210, which substantially surrounds end effector assembly 100. In this position, energy may be applied to distal tip 224 of rod member 220 to treat tissue, e.g., via activation of activation switch 4 (FIG. 1) in the monopolar mode. Distal tip 224 may be hook-shaped (as shown), or may define any other suitable configuration, e.g., linear, ball, circular, angled, etc.

Insulative sleeve 210 and rod member 220 of monopolar assembly 200 are coupled to one another via proximal hub 230 (FIG. 3), as will be described in greater detail below, such that insulative sleeve 210 and rod member 220 move in concert, e.g., together, with one another between their storage positions (FIGS. 2A and 2B), collectively the storage condition of monopolar assembly 200, and their deployed positions (FIG. 2D), collectively the deployed condition of monopolar assembly 200, upon selective translation of proximal hub 230 through housing 20 and relative to shaft 12 (see FIG. 1).

With reference again to FIG. 1, handle assembly 30 includes a movable handle 40 and a fixed handle 50. Fixed handle 50 is integrally associated with housing 20 and movable handle 40 is movable relative to fixed handle 50. Movable handle 40 is movable relative to fixed handle 50 between an initial position, wherein movable handle 40 is spaced from fixed handle 50, and a compressed position, wherein movable handle 40 is compressed towards fixed handle 50. A biasing member (not shown) may be provided to bias movable handle 40 towards the initial position. Movable handle 40 is ultimately connected to a drive assembly (not shown) disposed within housing 20 that, together, mechanically cooperate to impart movement of jaw members 110, 120 between the spaced-apart position (FIG. 2A), corresponding to the initial position of movable handle 40, and the approximated position (FIG. 2B), corresponding to the compressed position of movable handle 40. Any suitable drive assembly for this purpose may be provided such as, for example, the drive assembly disclosed in U.S. patent application Ser. No. 14/052,871, filed on Oct. 14, 2013, the entire contents of which are incorporated herein by reference.

Trigger assembly 60 includes trigger 62 that is operably coupled to knife 64 (FIG. 2B). Trigger 62 of trigger assembly 60 is selectively actuatable to advance knife 64 (FIG. 2B) from a retracted position, wherein knife 64 (FIG. 2B) is disposed proximally of jaw members 110, 120, to an extended position, wherein knife 64 (FIG. 2B) extends at least partially between jaw members 110, 120 and through knife channel(s) 125 (FIG. 2A) to cut tissue grasped between jaw members 110, 120.

Detailed below with respect to FIGS. 3-12, in conjunction with FIGS. 1-2D, are various embodiments of deployment mechanisms for selectively deploying monopolar assembly 200 (or similar monopolar assemblies). To the extent consistent, the various deployment mechanisms detailed hereinbelow, although described separately, may include any or all of the features of any or all of the other deployment mechanisms detailed hereinbelow, and may be utilized with forceps 10 or any other suitable surgical instrument.

Referring to FIGS. 3-7B, deployment mechanism 80 is configured for selectively translating proximal hub 230 relative to housing 20 and shaft 12 (FIG. 1) to thereby transition monopolar assembly 200 between its storage condition (FIGS. 2A and 2B) and its deployed condition (FIG. 2D). Deployment mechanism 80 generally includes a pair of actuators 82, first and second support members 150, 160 (second support member 160 has been removed from FIGS. 3, 7A, and 7B to better illustrate the components of deployment assembly 80), respectively, a clutch assembly 170, and a gear drive assembly 180. Each of these components will be detailed, in turn, below.

Actuators 82 are rotatably mounted on either side of housing 20 (FIG. 1) and are positioned to readily enable distal actuation thereof, e.g., clockwise rotation of either or both actuators 82 from the orientation shown in FIG. 1, to transition monopolar assembly 200 (FIGS. 2A-2D) between the storage condition (FIG. 2B) and the deployed condition (FIG. 2D). Actuators 82 are engaged about opposite ends of a pin 84 that extends between actuators 82 and through housing 20, support members 150, 160, and clutch assembly 170. More specifically, pin 84 is engaged with actuator plate 176 of clutch assembly 170 such that rotation of either or both actuators 82 effects corresponding rotation of pin 84 and, thus, actuator plate 176 of clutch assembly 170. A torsion spring 85 is disposed about pin 84 and configured to rotationally bias pin 84, e.g., in a counter-clockwise direction from the orientation shown in FIG. 1, thereby biasing actuators 82 towards their un-actuated positions shown in FIG. 1.

Figure 4:
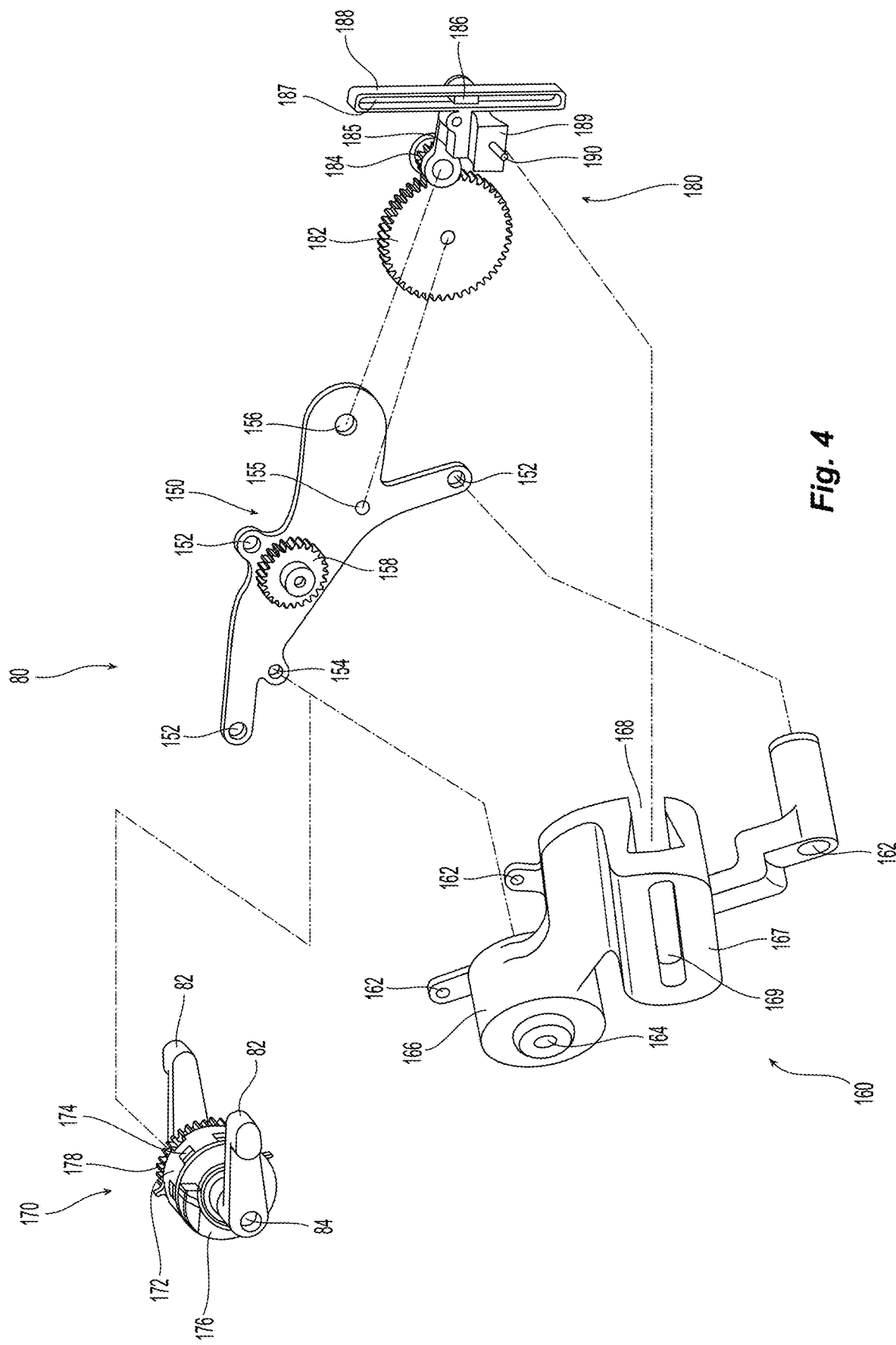
FIG. 4 is an exploded, perspective view of the deployment mechanism of FIG. 3.

Referring to FIG. 4, first and second support members 150, 160, respectively, are configured to support the various components of deployment mechanism 80 therebetween, retain the various components of deployment mechanism 80 in operable engagement with one another, and secure deployment mechanism 80 within housing 20. First support member 150 defines a plate-like configuration and includes a plurality of mounting aperture 152 defined therethrough. Second support member 160 likewise defines a plurality of mounting apertures 162 configured to align with mounting apertures 152 of first support member 150. Each pair of aligned mounting apertures 152, 162 is configured to receive a securement member 153 (FIG. 3), e.g., screw, pin, etc., for securing first and second support members 150, 160 to one another and/or to the interior of housing 20 (FIG. 3). First and second support members 150, 160 each further include a pin aperture 154, 164 that rotatably receives pin 84.

First support member 150 additionally includes first and second gear drive apertures 155, 156 defined therethrough for rotatably mounting first drive gear 182 and second drive gear 184 of gear drive assembly 180 to first support member 150. An intermediate gear 158 is rotatably mounted on first support member 150 and is positioned between pin aperture 154 and gear drive apertures 155, 156 such that, upon assembly, intermediate gear 158 operably couples clutch mechanism 170 and gear drive assembly 180 to one another for transmitting rotational motion therebetween, as detailed below.

Second support member 160 includes a cylindrical housing member 166 through which pin 84 extends and that is configured to rotatably receive actuator plate 176 of clutch mechanism 170. Second support member 160 further includes a guide body 167 defining a guide track 168 and a guide slot 169. As detailed below, guide body 167 is configured to guide translation of slider 189 of gear drive assembly 180 (see FIG. 6) and, thus, to guide the transition of monopolar assembly 200 between the storage condition (FIG. 2B) and the deployed condition (FIG. 2D).

Figure 5:
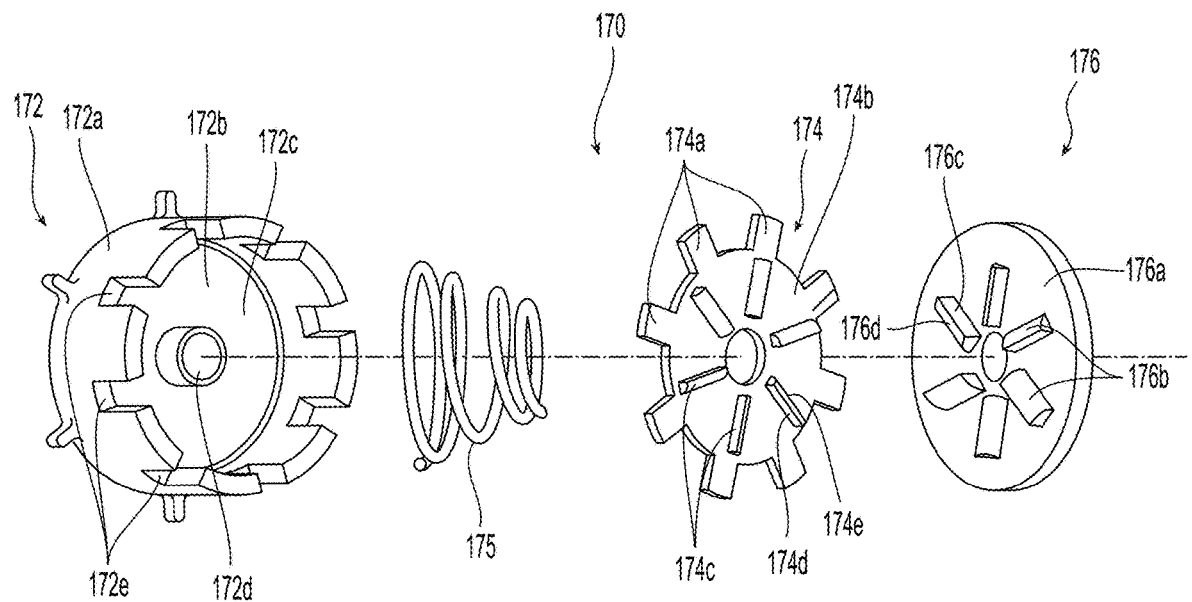
FIG. 5 is an exploded, perspective view of a clutch assembly of the deployment mechanism of FIG. 3.

Referring to FIGS. 3-5, clutch assembly 170 generally includes a base member 172, a clutch plate 174, a biasing member 175, an actuator plate 176, and an actuator gear 178. Actuator plate 176, as noted above, is secured about pin 84 and is rotatably received within cylindrical housing member 166 of second support member 160 such that, upon rotation of either or both actuators 82 to thereby rotate pin 84, actuator plate 176 is rotated within and relative to cylindrical housing member 166.

Base member 172 of clutch assembly 170 defines a generally cylindrical configuration having an annular wall 172a and an end wall 172b that cooperate to define a cavity 172c. End wall 172b defines a central aperture 172d configured to receive pin 84 therethrough for rotatably mounting base member 172 about pin 84. Actuator gear 178 is likewise rotatably disposed about pin 84 and is fixed to the outer surface of end wall 172b of base member 172 (or otherwise secured thereto) such that rotation of base member 172 effects corresponding rotation of actuator gear 178. Actuator gear 178 is disposed in meshed engagement with intermediate gear 158 such that rotation of actuator gear 178 effects opposite rotation of intermediate gear 158.

The open end of annular wall 172a of base member 172, e.g., the end of annular wall 172a opposite end wall 172b, defines a plurality of spaced-apart notches 172e arranged annularly thereabout. Clutch plate 174 includes a plurality of spaced-apart, radial protrusions 174a extending outwardly from the annular outer periphery therefrom and is shaped complementary to the open end of annular wall 172a of base member 172. Such a configuration allows each of the protrusions 174a to be received within one of the notches 172e defined within base member 172, thereby inhibiting relative rotation between clutch plate 174 and base member 172. Biasing member 175 is disposed within cavity 172c of base member 172 between end wall 172b and clutch plate 174 so as to bias clutch plate 174 apart from end wall 172b and into abutment with actuator plate 176, which is maintained adjacent clutch plate 174 via cylindrical housing member 166 of second support member 160.

Respective opposed surfaces 176a, 174b of actuator plate 176 and clutch plate 174, respectively, are maintained in abutment with one another under the bias of biasing member 175. Actuator plate 176 and clutch plate 174 each further include a plurality of one-way tabs 176b, 174c, respectively, disposed on the opposed surfaces 176a, 174b thereof that are arranged to define a circumferential pattern. Tabs 176b, 174c each include a surface 176c, 174d that extends perpendicularly from the respective opposed surface 176a, 174b and a curved surface 176d, 174e that gradually extends from the respective opposed surface 176a, 174b in a curved manner. Thus, relative rotation between actuator plate 176 and clutch plate 174 is only permitted in one direction, e.g., wherein curved surfaces 176d, 174e slide past one another (and clutch plate 176 is urged towards base member 172 against the bias of biasing member 175), and is inhibited in the second, opposite direction, e.g., wherein the perpendicular surfaces 176c, 174d abut one another. As a result of the above-detailed configurations of actuator plate 176 and clutch plate 174, rotation of either or both of actuators 82 in the actuating direction, e.g., clockwise from the orientation shown in FIG. 1, urges the perpendicular surfaces 176c of tabs 176b of actuator plate 176 into abutment with perpendicular surfaces 174d of tabs 174c of clutch plate 174 such that actuator plate 176 and clutch plate 174 and, thus, base member 172 and actuator gear 178, are rotated together with one another. On the other hand, return or release (under the bias of torsion spring 85) of either or both of actuators 82, e.g., counter-clockwise from the orientation shown in FIG. 1, permits curved surfaces 176d of tabs 176b of actuator plate 176 to slide over curved surfaces 174e of tabs 174c of clutch plate 174 such that actuator plate 176, pin 84, and actuators 82 are rotated relative to clutch plate 174, base member 172, and actuator gear 178 back to their respective initial positions without effecting rotation of clutch plate 174, base member 172, or actuator gear 178. Thus, clutch assembly 170 functions as a one-way drive mechanism wherein actuator gear 178 is rotatable in a single direction while actuators 82 are repeatedly actuatable and releasable to drive such rotation of actuator gear 178.

Referring still to FIGS. 3-5, gear drive assembly 180 includes a first drive gear 182 that is rotatably mounted on first support member 150, e.g., via a pin extending through first drive gear 182 and aperture 155, and is disposed in meshed engagement with intermediate gear 158 such that rotation of intermediate gear 158 effects rotation of first drive gear 182 in the opposite direction. First drive gear 182, in turn, is disposed in meshed engagement with a second drive gear 184 that is rotatably mounted on first support member 150, e.g., via a pin extending through second drive gear 184 and aperture 156.

An arm 185 is pinned to second drive gear 184 at a first end thereof such that rotation of second drive gear 184 effects corresponding rotation of arm 185. Arm 185 includes a hand 186 disposed at the second, opposite end of arm 185. Hand 186 is slidably received within a vertical slot 187 defined within an upright member 188 and is confined (relative to upright member 188) to vertical motion within vertical slot 187. A slider 189 is engaged to and extends distally from upright member 188. As a result of the above-configuration, as arm 185 is rotated through a first half of its full circumferential rotation, e.g., wherein arm 185 is moved in a generally distal direction, hand 186 is slid vertically through vertical slot 187 and pushes upright member 188 and, thus, slider 189 distally. On the other hand, as arm 185 is rotated through the second half of its full circumferential rotation, e.g., wherein arm 185 is moved in a generally proximal direction, hand 186 is slid vertically through vertical slot 187 to pull upright member 188 and, thus, slider 189, proximally.

Figure 6:
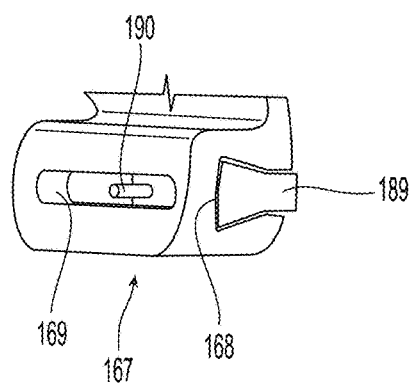
FIG. 6 is a perspective view of the guide assembly of the deployment mechanism of FIG. 3.
Figure 7B:
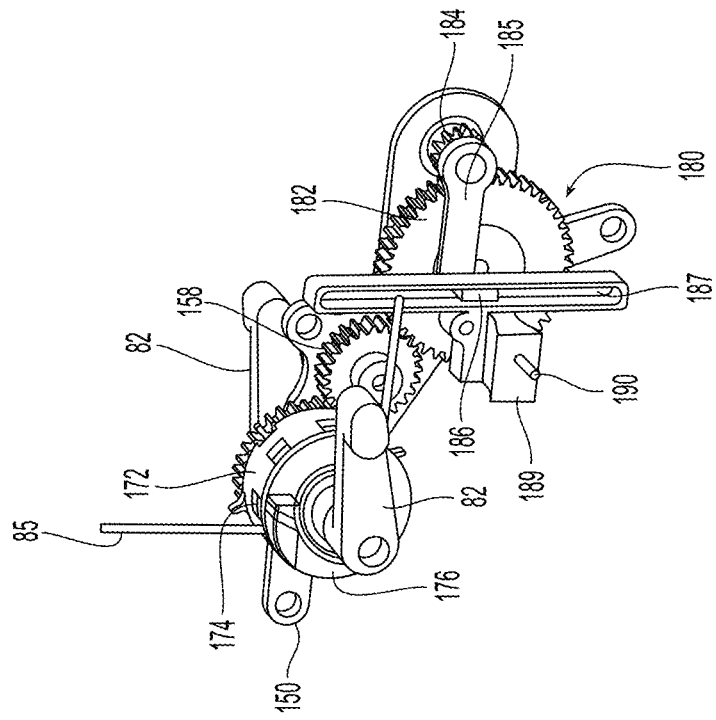
FIG. 7B is a perspective view of the deployment mechanism of FIG. 3 with the support portion removed and wherein the deployment mechanism is disposed in an actuated condition.
Figure 7A:
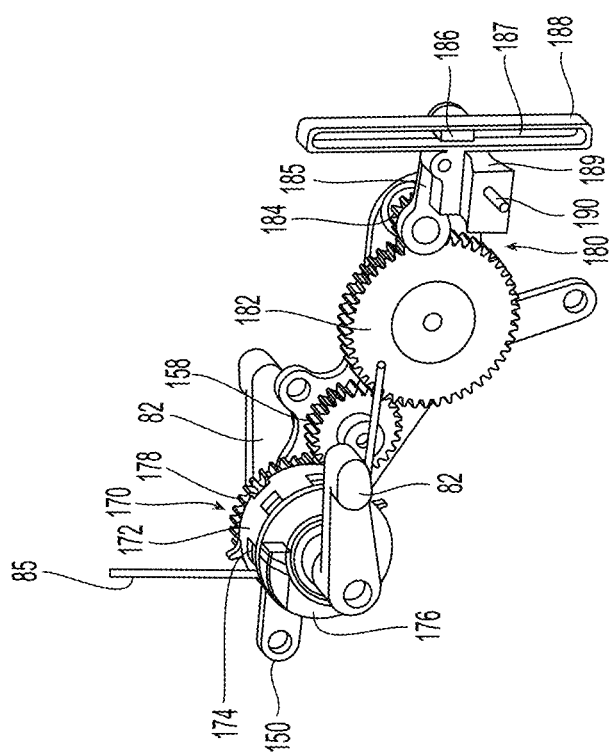
FIG. 7A is a perspective view of the deployment mechanism of FIG. 3 with a support portion removed and wherein the deployment mechanism is disposed in an un-actuated condition.

With additional reference to FIGS. 6, 7A, and 7B, slider 189 defines a transverse, cross-sectional configuration that is complementary to that of guide track 168 of guide body 167 of second support member 160 and is engaged therein such that slider 189 is confined to longitudinally translation through guide body 167. Slider 189 is engaged to or formed with proximal hub 230 of monopolar assembly 200 such that, as will be described in greater detail below, translation of slider 189 through guide body 167 urges monopolar assembly 200 through housing 20 and relative to shaft 12 (FIG. 1) between the storage condition (FIGS. 2A and 2B) and the deployed condition (FIG. 2D). More specifically, as second drive gear 184 rotates arm 185 through its first half of rotation wherein arm is moved in a generally distal direction, hand 185 urges upright member 188 and, thus, slider 189 distally, e.g., from the position shown in FIG. 7A to the position shown in FIG. 7B, to urge monopolar assembly 200 from the storage condition (FIGS. 2A and 2B) towards the deployed condition (FIG. 2D). On the other hand, as second drive gear 184 further rotates arm 185 through its second half of rotation (to complete a full rotation thereof) wherein arm is moved in a generally proximal direction, hand 185 urges upright member 188 and, thus, slider 189 proximally, e.g., from the position shown in FIG. 7B back to the position shown in FIG. 7A, to urge monopolar assembly 200 from the deployed condition (FIG. 2D) back towards the storage condition (FIGS. 2A and 2B).

Actuator gear 178, intermediate gear 158, first drive gear 182, and second drive gear 184 are configured to establish an advantageous gear ratio therebetween such that minimal actuation of actuators 82 is required to fully deploy and retract monopolar assembly 200. Specifically, it has been found that a gear ratio of less than or equal to about 1:3, e.g., wherein at most a 60 degree rotation of either or both actuators 82 effects a one-half rotation (180 degrees) of arm 185, which is sufficient to fully deploy or fully retract monopolar assembly 200. With momentary reference to FIG. 1, such a configuration, taking into account the ergonomic considerations of the movable handle 40, trigger 62, and actuators 82, enables a user to readily and effectively manipulate and utilize forceps 10 (FIG. 1) with a single hand, e.g., wherein the user's index finger is positioned to actuate trigger 62, the thumb is positioned to actuate one of the actuators 82 (in both right and left-handed use), and the remaining fingers are utilized to actuate movable handle 40. The push to deploy and push to retract (e.g., push-push) configuration of deployment mechanism 80 also facilitates this single-handed use in that retraction does not require an opposite motion and, thus, the user's thumb can be readily utilized for both deployment and retraction. Other ratios and configurations, including those where two-handed use is required or advantageous, are also contemplated.

Figure 8B:
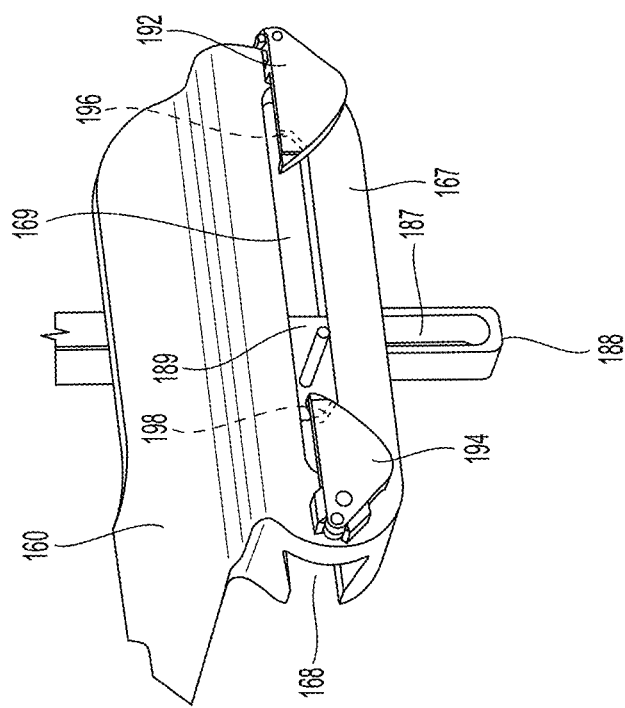
FIG. 8B is a perspective view of the guide assembly of the deployment mechanism of FIG. 3, wherein the guide member is approaching a distal locking member of the guide assembly.
Figure 8A:
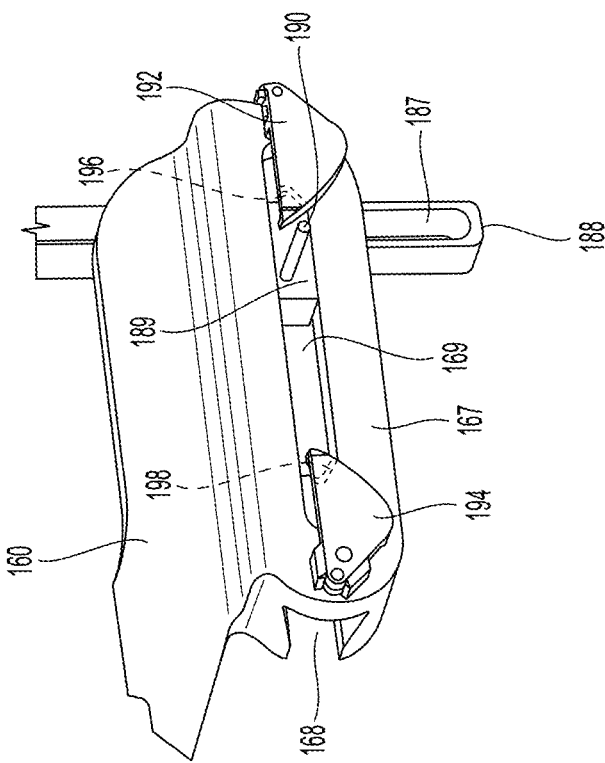
FIG. 8A is a perspective view of the guide assembly of the deployment mechanism of FIG. 3, wherein the guide member is approaching a proximal locking member.

Referring additionally to FIGS. 8A and 8B, slider 189 may further include a locking pin 190 extending transversely therefrom and guide body 167 may further include proximal and/or distal locking members 192, 194 for releasably locking deployment mechanism 80 in the actuated and/or un-actuated conditions, thereby releasably locking monopolar assembly 200 in the deployed and/or storage conditions. Locking pin 190, more specifically, extends transversely from slider 189 through guide slot 169 of guide body 167. Locking members 192, 194 are pivotably coupled to guide body 167 at a first end thereof and define locking tracks 196, 198, respectively, at the second, opposite ends thereof. Biasing members (not shown) may be provided to bias locking members 192, 194 towards an initial position. Upon translation of slider 189 to the proximal or distal position corresponding to the storage or deployed condition, respectively, of monopolar assembly 200, locking pin 190 enters the respective locking track 196, 198 and urges the respective locking member 192, 194 to pivot against its bias. Locking tracks 196, 198 include "catches" defined therein that are configured to releasably retain locking pin 190 once the proximal or distal position, respectively, has been achieved, thereby releasably locking monopolar assembly 200 in the deployed or storage condition. Release of locking pin 190 from locking tracks 196, 198 is effected by further translation of slider 189, e.g., distally from the distal position or proximally from the proximal position, thereby permitting locking pin 190 to exit the respective locking track 196, 198 and translate back in the opposite direction, while the locking member 192, 194 is returned under bias to its initial position. Thus, the "distal" and "proximal" positions of slider 189 are not the respective distal-most and proximal-most positions thereof, as a small amount of travel beyond these positions is provided to enable unlocking of locking pin 190.

Referring to FIGS. 1-8B, the use and operation of forceps 10 in both the bipolar mode, e.g., for grasping, treating (for example, sealing), and/or cutting tissue, and the monopolar mode, e.g., for electrical/electromechanical tissue treatment, is described. Turning to FIGS. 1 and 2A-2B, with respect to use in the bipolar mode, monopolar assembly 200 is maintained in the storage condition, wherein insulative sleeve 210 is positioned proximally of jaw members 110, 120, and distal tip 224 of energizable rod member 220 is disposed within insulative groove 126 of jaw flange 124 of jaw member 120. At this point, movable handle 40 is disposed in its initial position such that jaw members 110, 120 are disposed in the spaced-apart position (FIG. 2A). Further, trigger 62 of trigger assembly 60 remains un-actuated such that knife 64 (FIG. 2B) remains disposed in its retracted position.

Continuing with reference to FIGS. 1 and 2A-2B, with jaw members 110, 120 disposed in the spaced-apart position (FIG. 2A), end effector assembly 100 may be maneuvered into position such that tissue to be grasped, treated, e.g., sealed, and/or cut, is disposed between jaw members 110, 120. Next, movable handle 40 is depressed, or pulled proximally relative to fixed handle 50 such that jaw member 110 is pivoted relative to jaw member 120 from the spaced-apart position to the approximated position to grasp tissue therebetween (FIG. 2B). In this approximated position, energy may be supplied, e.g., via activation of switch 4, to surface 112 of jaw member 110 and/or surface 122 of jaw member 120 and conducted through tissue to treat tissue, e.g., to effect a tissue seal or otherwise treat tissue in the bipolar mode of operation. Once tissue treatment is complete (or to cut untreated tissue), knife 64 (FIG. 2B) may be deployed from within shaft 12 to between jaw members 110, 120, e.g., via actuation of trigger 62 of trigger assembly 60, to cut tissue grasped between jaw members 110, 120.

When tissue cutting is complete, trigger 62 may be released to return knife 64 (FIG. 2B) to the retracted position. Thereafter, movable handle 40 may be released or returned to its initial position such that jaw members 110, 120 are moved back to the spaced-apart position (FIG. 2A) to release the treated and/or divided tissue.

For operation of forceps 10 in the monopolar mode, jaw members 110, 120 are first moved to the approximated position, e.g., by depressing movable handle 40 relative to fixed handle 50. A lockout mechanism for inhibiting deployment of monopolar assembly 200 prior to movement of jaw members 110, 120 to the approximated positions may also be provided, such as the lockout mechanism described in U.S. patent application Ser. No. 14/276,465, filed on May 13, 2014, the entire contents of which are incorporated herein by reference. Once the approximated position has been achieved, monopolar assembly 200 may be deployed by transitioning deployment mechanism 80 from the un-actuated condition to the actuated condition. More specifically, in order to deploy monopolar assembly 200, either or both actuators 82 are rotated distally, e.g., clockwise from the orientation shown in FIG. 1, from the un-actuated position to the actuated position.

Rotation of either or both actuators 82, as detailed above, effects rotation of pin 84 and actuator plate 176, which engages clutch plate 174 and urges clutch plate 174, base member 172, and actuator gear 178 to rotate similarly as actuators 82. Being in meshed engagement, rotation of actuator gear 178 effects opposite rotation of intermediate gear 158 which, in turn, effects opposite rotation (relative to intermediate gear 158) of first drive gear 182. Rotation of first drive gear 182 effects opposite rotation of second drive gear 184 (relative to first drive gear 182) to thereby rotate arm 185 through its first half of rotation, e.g., distally from the position shown in FIG. 7A to the position shown in FIG. 7B. Such rotation of arm 185 slides hand 186 vertically through vertical slot 187 of upright member 188 and urges upright member 188 distally. Distal urging of upright member 188 urges slider 189 distally through guide track 168 of guide body 167, thereby translating proximal hub 230 of monopolar assembly 200 and, thus, insulative sleeve 210 and energizable rod member 220, distally relative to housing 20, shaft 12, and end effector assembly 100 from their storage positions (the storage condition of monopolar assembly 200) (FIG. 2B), to their deployed positions (the deployed condition of monopolar assembly 200) (FIG. 2D).

Upon full actuation of either or both actuators 82 to deploy monopolar assembly 200, the actuator(s) 82 can be released, allowing actuator plate 176 to rotate relative to clutch plate 174 (which remains relatively stationary) to thereby return the actuator(s) 82 to their initial position while monopolar assembly 200 remains disposed in the deployed condition via engagement of locking pin 190 within locking member 194 and drive gear assembly 180 remains disposed in the actuated condition shown in FIG. 7B.

With monopolar assembly 200 locked in the deployed condition, activation switch 4 may be actuated to supply energy to energizable rod member 220 to treat, e.g., dissect or otherwise treat, tissue. During application of energy to tissue via energizable rod member 220, forceps 10 may be moved relative to tissue, e.g., longitudinally, transversely, and/or radially, to facilitate electromechanical treatment of tissue.

At the completion of tissue treatment, either or both of actuators 82 may be actuated a subsequent time, e.g., either or both actuators 82 may once again be rotated distally from the un-actuated position to the actuated position. This subsequent, or re-actuation of either or both actuators 82, as detailed above, effects rotation of pin 84 and actuator plate 176, which engages clutch plate 174 and thereby urges clutch plate 174, base member 172, and actuator gear 178 to rotate. This rotation, in turn, rotates intermediate gear 158, first drive gear 182, and second drive gear 184 to thereby rotate arm 185 through the second half rotation, e.g., proximally from the position shown in FIG. 7B back to the position shown in FIG. 7A. Such rotation of arm 185 initially urges slider 189 distally to disengage locking pin 190 from locking member 194, thereby unlocking monopolar assembly 200 from the deployed condition, and slides hand 185 vertically through vertical slot 187 of upright member 188 while pulling upright member 188 proximally. Proximal pulling of upright member 188 pulls slider 189 proximally through guide track 168 of guide body 167, thereby translating proximal hub 230 of monopolar assembly 200 and, thus, insulative sleeve 210 and energizable rod member 220, proximally relative to housing 20, shaft 12, and end effector assembly 100 from their deployed positions (the deployed condition of monopolar assembly 200) (FIG. 2D) back to their storage positions (the storage condition of monopolar assembly 200) (FIG. 2B).

Upon return of slider 189 to the proximal position, locking pin 190 enters locking track 192 and is releasably engaged therein, thereby locking monopolar assembly 200 in the storage condition. Further, upon full re-actuation of either or both actuators 82 to deploy monopolar assembly 200, the actuator(s) 82 can be released, allowing actuator plate 178 to rotate relative to clutch plate 176 to thereby return the actuator(s) 82 to their initial position while monopolar assembly 200 remains disposed in the storage condition via engagement of locking pin 190 within locking member 192.

Figure 9B:
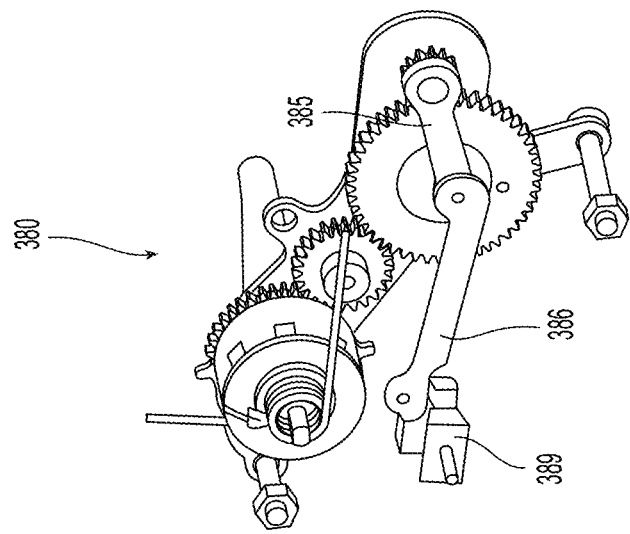
FIG. 9B is a perspective view of the deployment mechanism of FIG. 9A with the support member removed and wherein the deployment mechanism is disposed in an actuated condition.
Figure 9A:
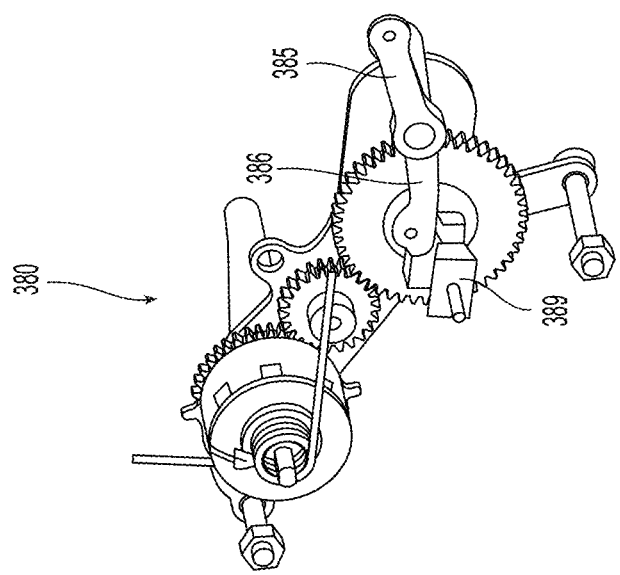
FIG. 9A is a perspective view another deployment mechanism provided in accordance with the present disclosure with a support member removed and wherein the deployment mechanism is disposed in an un-actuated condition.

Turning now to FIGS. 9A and 9B, another embodiment of a deployment mechanism provided in accordance with the present disclosure is shown generally as deployment mechanism 380. Deployment mechanism 380 is similar to and may include any or all of the features of deployment mechanism 80 (FIGS. 3-8B). Accordingly, for purposes of brevity, only the differences between deployment mechanism 380 and deployment mechanism 80 (FIGS. 3-8B) will be described in detail below.

Rather than providing a hand and upright member coupled to the second end of the arm, as detailed above with respect to deployment mechanism 80 (FIGS. 3-8B), deployment mechanism 380 includes a linkage bar 386 pivotably coupled to the second end of arm 385 at its first end and to slider 389 at its second end. In use, as arm 385 is rotated through its first half of rotation, e.g., in a generally distal direction, linkage bar 386 is pushed distally to thereby deploy monopolar assembly 200 (FIGS. 2A-2D). On the other hand, as arm 385 is rotated through its second half of rotation, e.g., in a generally proximal direction, linkage bar 386 is pulled proximally to thereby retract monopolar assembly 200 (FIGS. 2A-2D). The use and operation of deployment mechanism 380 is otherwise similar to that of deployment mechanism 80 (FIGS. 3-8B), detailed above.

Figure 10A:
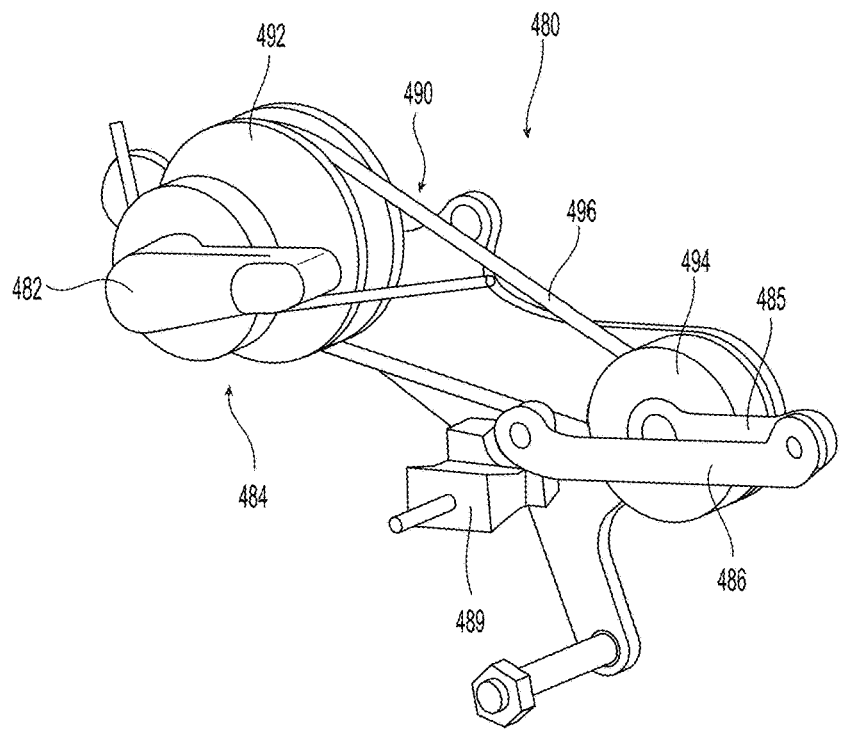
FIG. 10A is a perspective view another deployment mechanism provided in accordance with the present disclosure with a support portion removed and wherein the deployment mechanism is disposed in an un-actuated condition.
Figure 10B:
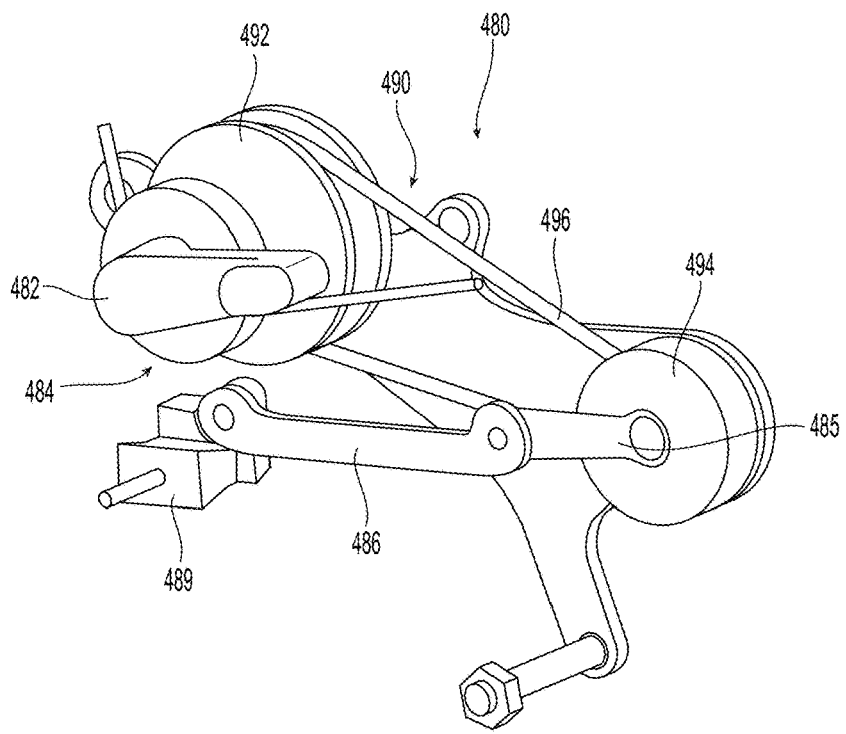
FIG. 10B is a perspective view of the deployment mechanism of FIG. 10A with the support portion removed and wherein the deployment mechanism is disposed in an actuated condition.

Turning now to FIGS. 10A and 10B, another embodiment of a deployment mechanism provided in accordance with the present disclosure is shown generally as deployment mechanism 480. Deployment mechanism 480 is similar to and may include any or all of the features of deployment mechanisms 80 (FIGS. 3-8B). Accordingly, for purposes of brevity, only the differences between deployment mechanism 480 and deployment mechanism 80 (FIGS. 3-8B) will be described in detail below.

Deployment mechanism 480, rather than providing a hand and upright member coupled to the second end of the arm, as detailed above with respect to deployment mechanism 80 (FIGS. 3-8B), includes a linkage bar 486 coupled to arm 485, similarly as detailed above with respect to deployment mechanism 380 (FIGS. 9A and 9B). However, it is also contemplated that deployment mechanism 480 be configured similar to deployment mechanism 80 (FIGS. 3-8B) in this manner, e.g., that deployment mechanism 480 include a hand and upright member coupled between the arm and slider.

Further, rather than providing a plurality of gear members for converting rotation of the actuators into longitudinal translation of the slider and, thus, deployment and retraction of monopolar assembly 200 (FIGS. 2A-2D), deployment mechanism 480 includes a pulley system 490. Pulley system 490 includes a first pulley wheel 492 coupled to clutch assembly 484 (similar to clutch assembly 170 of deployment mechanism 80 (FIGS. 3-8B)) and a second pulley wheel 494 having the first end of arm 485 coupled thereto. A pulley belt 496 is disposed about first and second pulley wheels 492, 494 are configured such that rotation of first pulley wheel 492, imparted thereto via clutch assembly 484, urges pulley belt 496 to rotate second pulley wheel 494. First and second pulley wheels 492, 494 and pulley belt 496 may be configured to establish an advantageous pulley ratio therebetween such that minimal actuation of actuators 482 is required to fully deploy and retract monopolar assembly 200 (FIGS. 2A-2D), similarly as detailed above with respect to deployment mechanism 80 (FIGS. 3-8B).

First pulley wheel 492 of pulley system 490, as mentioned above, is coupled to clutch assembly 484 of deployment mechanism 480 similarly as with actuator gear 178 of clutch assembly 170 of deployment mechanism 80 (see FIGS. 4 and 5). That is, first pulley wheel 492 is engaged with the clutch plate (not shown, similar to clutch plate 174 of deployment mechanism 80 (FIG. 4)) of the clutch assembly 484 such that rotation of actuator(s) 482 in a first direction effects rotation of first pulley wheel 492 and such that return of actuators 482 in the second, opposite direction is effected without moving first pulley wheel 492. Second pulley wheel 494 is coupled to arm 485 which is coupled to linkage bar 486 which, in turn, is coupled to slider 489 such that, similarly as detailed above, rotation of second pulley wheel 494 through a first half of rotation, e.g., generally distally, deploys monopolar assembly 200 (FIGS. 2A-2D) and such that further rotation of second pulley wheel 494 through a second half of rotation, e.g., generally proximally, retracts monopolar assembly 200 (FIGS. 2A-2D). The use and operation of deployment mechanism 480 is otherwise similar to that detailed above with respect to deployment mechanism 80 (FIGS. 3-8B).

Figure 11:
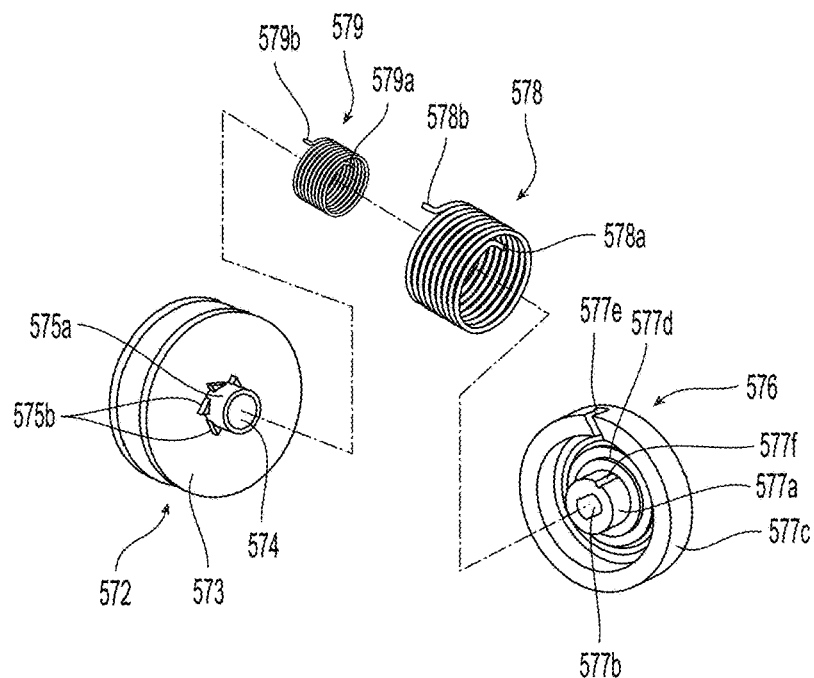
FIG. 11 is an exploded, perspective view of a clutch assembly provided in accordance with the present disclosure and configured for use with any of the deployment mechanisms detailed herein.
Figure 12:
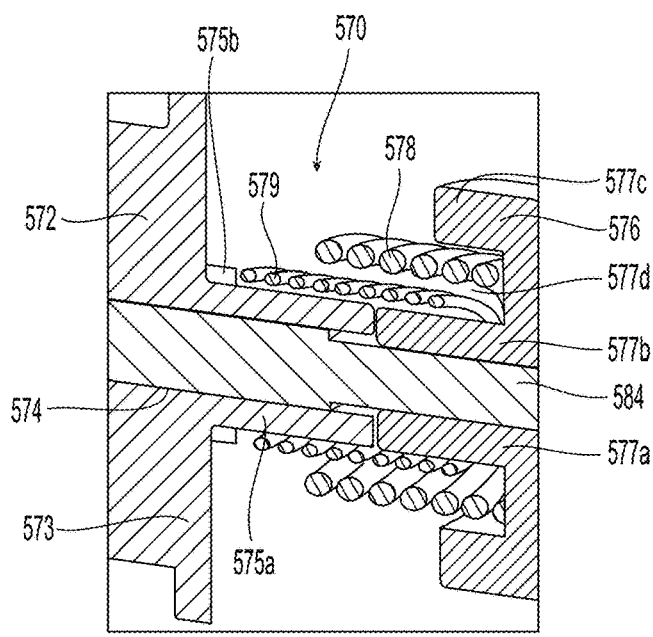
FIG. 12 is longitudinal, cross-sectional view of the clutch assembly of FIG. 11.

Referring to FIGS. 11 and 12, another embodiment of a clutch assembly 570 provided in accordance with the present disclosure is shown configured for use with deployment mechanism 480 (FIGS. 10A and 10B), although clutch assembly 570 may similarly be used with deployment mechanism 80 (FIGS. 3-8B) and/or deployment mechanism 380 (FIGS. 9A and 9B).

Clutch assembly 570 includes a first pulley wheel 572 that is similar to first pulley wheel 492 of deployment mechanism 480 (FIGS. 10A and 10B) except as detailed hereinbelow. However, in embodiments where clutch assembly 570 is utilized in deployment mechanism 80 (FIGS. 3-8B) and/or deployment mechanism 380 (FIGS. 9A and 9B), first pulley wheel 572 is instead an actuator gear similarly as detailed above with respect to those deployment mechanism. First pulley wheel 572 of clutch assembly 570 includes a body portion 573 defining an aperture 574 therethrough. A tubular extension 575a extends transversely from body portion 573 and is disposed about aperture 574 to define a lumen that is an extension of aperture 574. A plurality of radially-arranged, one-way teeth 575b are disposed about tubular extension 575a adjacent body portion 573.

Clutch assembly 570 further includes an actuator hub 576, and first and second biasing members 578, 579, respectively. Actuator hub 576 defines an inner member 577a that is configured to abut tubular extension 575a of first pulley wheel 572 and includes an aperture 577b extending therethrough. Aperture 577b is configured to receive a pin 584 (similar to pin 84 (FIG. 3)) to engage actuator hub 576 with the actuator (not shown, similar to actuators 82 (FIG. 3). Pin 584 extends through and is rotatably disposed within aperture 574 of first pulley wheel 572 such that actuator hub 576 and pin 584 are together rotatable relative to first pulley wheel 572. Actuator hub 576 further includes an outer annular member 577c spaced-apart from inner member 577a to define a ring-shaped recess 577d therebetween.

As detailed below, first biasing member 578 is provided to return the actuator to the initial position after actuation, while second biasing member 579, in conjunction with one-way teeth 575b, provide the clutch functionality of clutch assembly 570 that enables actuation of the actuator to drive first pulley wheel 572, while first pulley wheel 572 is retained in position upon return of the actuator to is initial position. First biasing member 578 includes a first end 578a that extends into recess 577d and is engaged within a slot 577e defined within outer annular member 577c. Likewise, second biasing member 579 includes a first end 579a that extends into recess 577d and is engaged within a slot 577f defined within inner member 577a. Thus, first ends 578a, 579a of first and second biasing members 578, 579, respectively, are rotationally fixed relative to actuator hub 576. First and second biasing members 578, 579 are configured as coiled torsion springs wherein first biasing member 578 defines a larger diameter than second biasing member 579 so as to enable first biasing member 578 to be positioned about second biasing member 579 (see FIG. 12).

Second end 578b of first biasing member 578 is fixed (e.g., secured to one of the support members of the deployment mechanism and/or the housing of the forceps) such that rotation of actuator hub 576 in response to actuation of one or both of the actuators torques first biasing member 578. Upon release of the actuator(s), the energy built up in first biasing member 578 is released, thereby urging the actuator(s) and actuator hub 576 back to their respective initial positions.

Second end 579b of second biasing member 579 is operably positioned relative to one-way teeth 575b of first pulley wheel 572 such that rotation of actuator hub 576 in a first direct, e.g., in response to actuation of one or both of the actuators, applies torque to second biasing member 579 and urges second end 579b of second biasing member 579 to rotate into contact with the perpendicular surface of one of the one-way teeth 575b of first pulley wheel 572 to likewise urge first pulley wheel 572 to rotate. Similarly as noted above with respect to deployment mechanism 480 (FIGS. 10A and 10B), rotation of first pulley wheel 572 ultimately effects deployment or retraction of monopolar assembly 200 (FIGS. 2A-2D). Upon release of the actuator(s), the energy built up in second biasing member 579 is released, thereby urging second end 579b of second biasing member 579 to rotate back towards its initial position. During such rotation, second end 579b of second biasing member 579 cams over the angled surfaces of one-way teeth 575b such that second biasing member 579 is returned to its initial position without effecting rotation of first pulley wheel 572.

The various embodiments disclosed herein may also be configured to work with robotic surgical systems and what is commonly referred to as "Telesurgery." Such systems employ various robotic elements to assist the surgeon in the operating room and allow remote operation (or partial remote operation) of surgical instrumentation. Various robotic arms, gears, cams, pulleys, electric and mechanical motors, etc. may be employed for this purpose and may be designed with a robotic surgical system to assist the surgeon during the course of an operation or treatment. Such robotic systems may include remotely steerable systems, automatically flexible surgical systems, remotely flexible surgical systems, remotely articulating surgical systems, wireless surgical systems, modular or selectively configurable remotely operated surgical systems, etc.

The robotic surgical systems may be employed with one or more consoles that are next to the operating theater or located in a remote location. In this instance, one team of surgeons or nurses may prep the patient for surgery and configure the robotic surgical system with one or more of the instruments disclosed herein while another surgeon (or group of surgeons) remotely control the instruments via the robotic surgical system. As can be appreciated, a highly skilled surgeon may perform multiple operations in multiple locations without leaving his/her remote console which can be both economically advantageous and a benefit to the patient or a series of patients.

The robotic arms of the surgical system are typically coupled to a pair of master handles by a controller. The handles can be moved by the surgeon to produce a corresponding movement of the working ends of any type of surgical instrument (e.g., end effectors, graspers, knifes, scissors, etc.) which may complement the use of one or more of the embodiments described herein. The movement of the master handles may be scaled so that the working ends have a corresponding movement that is different, smaller or larger, than the movement performed by the operating hands of the surgeon. The scale factor or gearing ratio may be adjustable so that the operator can control the resolution of the working ends of the surgical instrument(s).

The master handles may include various sensors to provide feedback to the surgeon relating to various tissue parameters or conditions, e.g., tissue resistance due to manipulation, cutting or otherwise treating, pressure by the instrument onto the tissue, tissue temperature, tissue impedance, etc. As can be appreciated, such sensors provide the surgeon with enhanced tactile feedback simulating actual operating conditions. The master handles may also include a variety of different actuators for delicate tissue manipulation or treatment further enhancing the surgeon's ability to mimic actual operating conditions.

From the foregoing and with reference to the various drawing figures, those skilled in the art will appreciate that certain modifications can also be made to the present disclosure without departing from the scope of the same. While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed is:

1. An actuation mechanism for actuating a feature of a surgical instrument, the actuation mechanism comprising:
    an actuator configured to provide a rotational input;
    a drive assembly configured to receive the rotational input from the actuator and, based thereon, provide a rotational output;
    an arm configured to receive the rotational output from the drive assembly and to rotate in response thereto, the arm having a hand disposed at a free end portion of the arm;
    a track that encircles the hand, the hand positioned to translate through the track; and
    a slider coupled to the arm such that, in response to rotation of the arm and movement of the hand through the track, the slider is translated to thereby actuate the feature of the surgical instrument,
    wherein a ratio of a degree of rotation of the actuator relative to a degree of rotation of the arm is less than or equal to 1:3,
    wherein the track defines a slot, the hand slidably engaged within the slot, and
    wherein the slider is coupled to the track such that rotation of the arm moves the hand vertically along the slot to translate the track between proximal and distal positions to thereby urge the slider to translate between proximal and distal positions.

2. The actuation mechanism according to claim 1, wherein the drive assembly includes:
    a first pulley wheel configured to receive the rotational input;
    a second pulley wheel configured to provide the rotational output; and
    a pulley belt operably coupled between the first and second pulley wheels and configured to transfer rotation of the first pulley wheel to the second pulley wheel.

3. The actuation mechanism according to claim 1, wherein the drive assembly includes:
    a first gear configured to receive the rotational input;
    a second gear configured to provide the rotational output; and
    an intermediate gear disposed in meshed engagement with each of the first and second gears and configured to transfer rotation of the first gear to the second gear.

4. The actuation mechanism according to claim 1, further comprising a clutch assembly coupled between the actuator and the drive assembly such that the rotational input in a first rotational direction is provided to the drive assembly and such that rotational of the actuator in a second, opposite rotational direction is not provided to the drive assembly.

5. The actuation mechanism according to claim 1, further comprising:
    a linkage bar having a first end portion and a second end portion, the first end portion pivotably coupled to a free end portion of the arm, wherein the slider is pivotably coupled to the second end portion of the linkage such that rotation of the arm moves the linkage to thereby urge the slider to translate.

6. The actuation mechanism of claim 1, wherein the track defines a closed vertical slot that receives the hand therein, the hand slidably movable through the closed vertical slot between vertically offset positions.

7. The actuation mechanism of claim 1, wherein the track moves relative to the drive assembly.

* * * * *